US011116836B2

(12) United States Patent
Tian et al.

(10) Patent No.: US 11,116,836 B2
(45) Date of Patent: Sep. 14, 2021

(54) BIVALENT VACCINE COMPOSITION FOR PREVENTING AND/OR TREATING PORCINE CIRCOVIRUS INFECTIONS AND PREPARATION METHOD AND USE THEREOF

(71) Applicant: PULIKE BIOLOGICAL ENGINEERING, INC., Henan (CN)

(72) Inventors: Kegong Tian, Henan (CN); Xiangdong Li, Henan (CN); Yan Xiao, Henan (CN); Xiangfeng Xi, Henan (CN); Jinzhong Sun, Henan (CN); Xuke Zhang, Henan (CN)

(73) Assignee: PULIKE BIOLOGICAL ENGINEERING, INC., Henan (CN)

( * ) Notice: Subject to any disclaimer, the term of this patent is extended or adjusted under 35 U.S.C. 154(b) by 16 days.

(21) Appl. No.: 16/620,685

(22) PCT Filed: Dec. 25, 2017

(86) PCT No.: PCT/CN2017/118343
§ 371 (c)(1),
(2) Date: Dec. 9, 2019

(87) PCT Pub. No.: WO2018/223668
PCT Pub. Date: Dec. 13, 2018

(65) Prior Publication Data

US 2021/0023203 A1 Jan. 28, 2021

(30) Foreign Application Priority Data

Jun. 9, 2017 (CN) ........................ 201710433755.4

(51) Int. Cl.
*A61K 39/295* (2006.01)
*A61P 31/20* (2006.01)

(52) U.S. Cl.
CPC ........... *A61K 39/295* (2013.01); *A61P 31/20* (2018.01)

(58) Field of Classification Search
CPC .......... A61K 39/295; A61K 2039/5252; A61K 2039/55566; A61K 2039/552; A61K 2039/70; A61K 39/12; A61P 31/20; C12N 2750/10034
See application file for complete search history.

(56) References Cited

U.S. PATENT DOCUMENTS 10,869,919 B2 * 12/2020 Tian ...................... A61K 39/12

FOREIGN PATENT DOCUMENTS

| | | | | | |
|---|---|---|---|---|---|
| CN | 104334186 | A | | 2/2015 | |
| CN | 104450559 | A | | 3/2015 | |
| CN | 104474542 | A | | 4/2015 | |
| CN | 107854688 | A | * | 3/2018 | |
| WO | WO 2017/066772 | A1 | | 4/2017 | |
| WO | WO-2018233264 | A1 | * | 12/2018 | ............ C12N 15/62 |

OTHER PUBLICATIONS

Fenaux M, Opriessnig T, Halbur PG, Elvinger F, Meng XJ. Two amino acid mutations in the capsid protein of type 2 porcine circovirus (PCV2) enhanced PCV2 replication in vitro and attenuated the virus in vivo. J Virol. Dec. 2004;78(24): 13440-6.*
International Search Report dated Mar. 29, 2018 issued in PCT/CN2017/118343.

* cited by examiner

*Primary Examiner* — Rachel B Gill
(74) *Attorney, Agent, or Firm* — Scully, Scott, Murphy & Presser, P.C.

(57) ABSTRACT

A vaccine composition for preventing and/or treating porcine circovirus infection is described, which comprises an immunogenic amount of porcine circovirus type 3 antigen, an immunogenic amount of porcine circovirus type 2 antigen and a pharmaceutically acceptable carrier. The vaccine composition can not only prevent and/or treat related diseases caused by infection or mixed infection of different gene subtypes of porcine circovirus, but also have immunoprotective effects against strains of different geographical origins.

12 Claims, No Drawings

BIVALENT VACCINE COMPOSITION FOR PREVENTING AND/OR TREATING PORCINE CIRCOVIRUS INFECTIONS AND PREPARATION METHOD AND USE THEREOF

TECHNICAL FIELD

The disclosure relates to a bivalent vaccine composition for preventing and/or treating porcine circovirus infection and preparation method and use thereof, belonging to the field of animal virology.

BACKGROUND

A porcine circovirus (PCV) is a single-stranded ring-shaped DNA virus with a length of genomic sequence of about 1.7 kb, making it one of the smallest animal DNA viruses. Two types of PCV have been identified, namely porcine circovirus type 1 (PCV1) and porcine circovirus type 2 (PCV2). PCV1, which was first identified in PK cell culture as a contaminant in 1974, is not pathogenic to pigs. PCV2 first reported in 1998 can cause porcine circovirus associated diseases (PCVAD) in pigs under clinical conditions, mainly causing postweaning multisystemic wasting syndrome (PMWS), pneumonia, porcine dermatitis and nephropathy syndrome, and reproductive disorders, of which manifestations include respiratory dysfunction, urinary dysfunction, intestinal dysfunction, lymphatic dysfunction, cardiovascular dysfunction, neurological dysfunction, reproductive system dysfunction and skin dysfunction, which has caused significant economic losses to pig farming worldwide.

Clinically, with the widespread application of PCV2 vaccines, the mutation rate of PCV2 is accelerated under the immune pressure, and a strain with a new gene subtype between PCV2b and PCV2d begins to prevail, and such virus is characterized by the existence of mutation or recombination of different gene subtypes in ORF2 gene. Due to the prevalence of the strain with a new gene subtype of PCV2, there is a difference between the antigen of the new gene subtype and that of the existing gene subtypes, while the existing commercial vaccines are prepared by using PCV2a or PCV2b as vaccine strains, and can not completely protect the newly prevalent PCV2 strain.

In a case of reproductive disorders in pigs, a porcine circovirus strain with a length of genomic sequence of 2.0 kb was isolated and confirmed as the pathogenic pathogen. As further confirmed by subsequent experiments, the sequence of the strain shared less than 50% identity at the nucleotide- or amino acid-level (nt- or aa-level) to those of any reported circoviruses. According to the standard from the International Committee on Taxonomy of Viruses, ICTV, virus members in the same species of the genus Circovirus should share >75% nt-identity over their entire genome, and >70% aa-identity in the Cap protein. It is therefore confirmed as a new species (PCV3) in the genus Circovirus.

The systemic disease caused by PCV2 has already broken out in a sporadic state as early as 1985. The disease broke out large-scale in the late 1990s due to failure to pay attention. The new Porcine circovirus has similar etiological properties to PCV2 in terms of porcine dermatitis and nephropathy syndrome (PDNS) and reproductive disorders, and the protein homology between PCV2 and PCV3 is very low. PCV3 cannot be effectively prevented and cross-protected by PCV2 vaccine.

The mixed infection between the new porcine circovirus and PCV2 further aggravates the complexities of clinical PCV infection, so the preparation of new vaccine compositions for this new clinical epidemic is important for disease control in pig farms.

SUMMARY OF THE INVENTION

In order to solve the deficiencies of the prior art, the present invention provides a vaccine composition for preventing and/or treating mixed infection of porcine circovirus, which can provide effective protection against mixed infection of different types of porcine circovirus, exhibiting significant immunological properties.

It is an object of the present invention to provide a vaccine composition for preventing and/or treating porcine circovirus infection, which comprises an immunogenic amount of porcine circovirus type 3 antigen, an immunogenic amount of porcine circovirus type 2 antigen and a pharmaceutically acceptable carrier.

Another object of the present invention is to provide a vaccine composition for preventing and/or treating mixed infection of different porcine circoviruses and different gene subtypes of porcine circovirus type 2.

Another object of the present invention is to provide a vaccine composition for preventing and/or treating porcine circovirus infection of different geographical origins.

Another object of the present invention is to provide a method for preparing a vaccine composition for preventing and/or treating porcine circovirus infection, comprising: step (1) respectively proliferating porcine circovirus type 3 virus and porcine circovirus type 2 virus; step (2) inactivating the porcine circovirus type 3 virus and the proliferated porcine circovirus type 2 virus; step (3) mixing the antigens of the inactivated porcine circovirus type 3 virus and the inactivated porcine circovirus type 2 virus, which is then added with an adjuvant and emulsified.

Another object of the present invention is to provide a use of the above vaccine composition in preparing a medicine for preventing and/or treating a disease associated with porcine circovirus infection.

The invention has the advantages that:

(1) The vaccine composition of the present disclosure has good immunogenicity, can stimulate the body to quickly generate immunity after one-time immunization, effectively prevent the attack of epidemic strains, and has excellent protection effect; the vaccine composition of the present disclosure can achieve good immune protection effect at lower antigen content, and further reduce production costs;

(2) the vaccine composition of the present disclosure, firstly prepared by the porcine circovirus type 3 strain and porcine circovirus type 2 strain, can not only carry out immune protection on infection or mixed infection of the porcine circovirus type 2 strain and the porcine circovirus type 3 strain, but also protect against infection or mixed infection of different gene subtypes of porcine circovirus type 2 strains;

(3) The vaccine of the present disclosure can provide complete protection against mixed infection of the porcine circovirus type 3 strain and the porcine circovirus type 2 strain of different geographical origins, and have an ability to provide broad-spectrum protection;

DETAILED DESCRIPTION

Hereinafter, embodiments of the present disclosure will be described.

Porcine circovirus type 3 is a circovirus with a length of genomic sequence of 2.0 kb, the sequence of which shares less than 50% identity at the nt- or aa-level to those of any reported circoviruses and is a new species of porcine circovirus. It can cause porcine dermatitis and nephropathy syndrome, proliferative necrotizing pneumonia, reproductive disorders, and inflammatory responses to the heart and multiple systems.

"PCV 2new gene subtype" refers to a new PCV2 gene subtype with the existence of mutation or recombination of different gene subtypes in ORF2 gene thereof, which has a PCV2b tag sequence, but forms an independent branch in genetic evolution analysis. Clinical characteristics of a pig after being infected with the gene subtype strain are as follows: persistent high temperature, loss of appetite, depression, rough hair coat, emaciation and low growth rate, and different levels of lung consolidation, lymphadenectasis and kidney necrosis shown in necropsy results.

The present invention relates to a vaccine composition for preventing and/or treating porcine circovirus infection, wherein the vaccine composition comprises an immunogenic amount of porcine circovirus type 3 antigen, an immunogenic amount of porcine circovirus type 2 antigen and a pharmaceutically acceptable carrier.

The vaccine composition prepared for the mixed infection of porcine circovirus may comprise an immunogenic amount of inactivated antigen or attenuated whole virus antigen of porcine circovirus type 3 or a culture thereof, an immunogenic amount of inactivated antigen or attenuated whole virus antigen of porcine circovirus type 2 or a culture thereof, and a pharmaceutically acceptable carrier.

The porcine circovirus type 3 antigen and the porcine circovirus type 2 antigen comprised in the vaccine composition have good immunogenicity, can quickly activate immune response at low content, and protect pigs from being attacked by strains.

The "vaccine composition" refers to a pharmaceutical composition having immunogenicity against porcine circovirus type 3 and porcine circovirus type 2. The pharmaceutical composition can induce, stimulate or enhance the immune response of pigs to porcine circovirus type 3 and porcine circovirus type 2.

The "inactivated vaccine", also called non-living vaccine, refers to suspension of inactivated virus used as an antigen for producing immunity. Examples of inactivated vaccines include whole-virus vaccines and split-virus vaccines. By using known methods, it is easy to produce inactivated vaccines. For instance, inactivated whole-virus vaccines can be obtained by treatment with formaldehyde solution. Split-virus vaccines can be prepared with virus envelopes after treatment with ether.

"Attenuated whole-virus antigen" refers to a virus which still can reproduce in the host or on the cells while their virulence has been weakened. As used herein, the term "attenuated" refers to artificially reducing the virulence of pathogens via mutation of gene such that pathogens are deprived of pathogenicity but maintain immunogenicity. Generally attenuation can be achieved by UV irradiation, chemical processing or continuous high-order subculturing in vitro, or by artificial alteration of gene via, for example, the deletion of some specific nucleotides in the given sequence causing the virulence weaken.

According to an embodiment of the present disclosure, in the vaccine composition of the present disclosure, the porcine circovirus type 3 antigen is an antigen of a porcine circovirus type 3 SG strain of which the accession number is CCTCC NO. V201712; and the porcine circovirus type 2 antigen is an antigen of a porcine circovirus type 2 HH3 strain of which the accession number is CCTCC NO. V201726.

The porcine circovirus type 3 SG strain was deposited in the China Center for Type Culture Collection on Mar. 23, 2017, of which the accession number is CCTCC NO. V201712 and the address is Wuhan University, Wuhan, China.

The new porcine circovirus type 2 provided by the invention with a whole length of genomic sequence of 1768 nucleotides, has a PCV2b tag sequence, but forms an independent branch in genetic evolution analysis, and is a new PCV2 gene subtype with the existence of mutation or recombination of different gene subtypes in ORF2 gene thereof. The porcine circovirus type 2 HH3 strain was deposited in the China Center for Type Culture Collection on Jun. 4, 2017, of which the accession number is CCTCC NO. V201726 and the address is Wuhan University, Wuhan, China.

The strain used in the vaccine composition has good immunogenicity, through which the prepared vaccine composition can effectively stimulate an immune system at low content, the immune effect can be quickly generated by one-time immunization, the body can be completely protected, and the protection rate can reach 100%.

The vaccine composition of the invention can completely protect against single infection and mixed infection of different gene subtypes of PCV2 and PCV3.

The vaccine composition can provide effective protection against strains from different geographical origins, and the application scope of the vaccine is expanded.

As an embodiment of the present disclosure, in the vaccine composition of the present disclosure, the antigen of the porcine circovirus type 3 SG strain is an inactivated whole-virus antigen of the porcine circovirus type 3 virus SG strain or the culture thereof, the culture of the porcine circovirus type 3 SG strain is a culture which has been subcultured for more than one passage; the antigen of the porcine circovirus type 2 HH3 strain is an inactivated whole-virus antigen of the porcine circovirus type 2 HH3 strain or the culture thereof, the culture of the porcine circovirus type 2 HH3 strain is a culture which has been subcultured for more than one passage.

The "culture" refers to cultures of different passages of the virus, known to those skilled in the art, which may only have minute variations in gene sequences from one passage to another.

According to a preferred embodiment of the present disclosure, in the vaccine composition of the present disclosure, the culture of the porcine circovirus type 3 SG strain is a culture which has been subcultured for more than five passages, the culture of the porcine circovirus type 2 HH3 strain is a culture which has been subcultured for more than five passages.

According to a more preferred embodiment of the present disclosure, in the vaccine composition of the present disclosure, the culture of the porcine circovirus type 3 SG strain is a culture which has been subcultured for 5 to 55 passages, the culture of the porcine circovirus type 2 HH3 strain is a culture which has been subcultured for 5 to 48 passages.

As an embodiment of the present disclosure, in the vaccine composition of the present disclosure, the inactivated antigen of the porcine circovirus type 3 SG strain or the culture thereof is a split-type antigen of the porcine circovirus type 3 virus SG strain. The inactivated antigen of the porcine circovirus type 2 HH3 strain or the culture thereof is a split-type antigen of the porcine circovirus type 2 HH3 strain.

The amount of the ingredient or component of the composition of the disclosure is preferably a therapeutically effective amount. The therapeutically effective amount refers to the amount necessary to exert the immunological effects of the composition in the host to which the composition is administered without causing excessive side effects. The precise amounts of ingredients used and of compositions to be administered will vary depending on factors such as the type of disease being treated, the type and age of the animal to be treated, the mode of administration, and other ingredients in the composition.

As an embodiment of the present disclosure, in the vaccine composition of the present disclosure, the inactivated whole-virus antigen content of the porcine circovirus type 3 SG strain or the culture thereof is equal to or more than $10^{5.0}$ $TCID_{50}$/ml before inactivation, the inactivated whole-virus antigen content of the porcine circovirus type 2 HH3 strain or the culture thereof is equal to or more than $10^{5.0}$ $TCID_{50}$/ml before inactivation.

The inactivated whole-virus antigen of the porcine circovirus type 3 SG strain or the culture thereof in the vaccine composition of the present disclosure has good immunogenicity. It can stimulate the body to quickly generate the immune effect by one-time immunization. Even when inactivated whole-virus antigen of the porcine circovirus type 3 SG strain or the culture thereof in the vaccine composition is used at a content of $10^{5.0}$ $TCID_{50}$/ml before inactivation, the body can achieve good immune protection, and the protection rate can reach 100%.

The inactivated whole-virus antigen of the porcine circovirus type 2 HH3 strain or the culture thereof in the vaccine composition of the present disclosure has good immunogenicity. It can stimulate the body to quickly generate the immune effect by one-time immunization. Even when the inactivated whole-virus antigen of the porcine circovirus type 2 HH3 strain or the culture thereof in the vaccine composition is used at a content of $10^{5.0}$ $TCID_{50}$/ml before inactivation, the body can achieve good immune protection, and the protection rate can reach 100%.

As a preferred embodiment of the present disclosure, in the vaccine composition of the present disclosure, the inactivated whole-virus antigen content of the porcine circovirus type 3 SG strain or the culture thereof is within a range of $10^{5.0}$ to $10^{7.0}$ $TCID_{50}$/ml before inactivation, and the inactivated whole-virus antigen content of the porcine circovirus type 2 HH3 strain or the culture thereof is within a range of $10^{5.0}$ to $10^{7.0}$ $TCID_{50}$/ml before inactivation.

As a preferred embodiment of the present disclosure, in the vaccine composition of the present disclosure, the inactivated whole-virus antigen content of the porcine circovirus type 3 SG strain or the culture thereof is $10^{6.0}$ $TCID_{50}$/ml before inactivation, and the inactivated whole-virus antigen content of the porcine circovirus type 2 HH3 strain or the culture thereof is $10^{6.0}$ $TCID_{50}$/ml before inactivation.

In the vaccine composition of the present disclosure, the range of the inactivated whole-virus antigen content of the porcine circovirus type 3 SG strain or the culture thereof may further be selected from a range of $10^{5.0}$ to $10^{6.0}$ $TCID_{50}$/ml, or a range of $10^{6.0}$ to $10^{7.0}$ $TCID_{50}$/ml, and the range of the inactivated whole-virus antigen content of the porcine circovirus type 2 HH3 strain or the culture thereof may further be selected from a range of $10^{5.0}$ to $10^{6.0}$ $TCID_{50}$/ml, or a range of $10^{6.0}$ to $10^{7.0}$ $TCID_{50}$/ml.

As one embodiment of the present invention, in the vaccine composition of the present invention, the pharmaceutically acceptable carrier is an adjuvant, and the adjuvant includes white oil, oil Drake, and other animal oils, vegetable oils or mineral oil; or aluminum hydroxide, aluminum phosphate, and other metal salts; or Montanide™ Gel, carbomer, squalane or squalene, ISA206 adjuvant, saponin, water-in-oil emulsion, oil-in-water emulsions, water-in-oil-in-water emulsion.

As one embodiment of the present invention, in the vaccine composition of the present invention, the adjuvant is Montanide™ Gel.

The amount of adjuvant that is suitable for the composition of the present disclosure is preferably an effective amount. The "effective amount" refers to a required amount of the adjuvant that is necessary or sufficient to exert an immunological effect in the host in combination with the antigen of the disclosure without causing excessive side effects. The precise amount of adjuvant to be administrated varies depending on factors such as the components employed and the type of diseases being treated, the type and age of the animal to be treated, the mode of administration, and other ingredients in the composition.

As one embodiment of the present invention, in the vaccine composition of the present invention, the adjuvant is used in an amount of 5 to 20% by volume.

As a preferred embodiment of the present disclosure, in the vaccine composition of the present disclosure, the adjuvant is used in an amount of 10% by volume.

Vaccine compositions of the disclosure may be formulated using conventional techniques, preferably together with a veterinarily acceptable carrier. For example, oil can help to stabilize the formulation, and additionally act as a vaccine adjuvant.

Oil adjuvants can be either naturally or synthetically obtained.

The term "adjuvant" refers to a substance that is added to the composition of the present disclosure to increase the immunogenicity of the composition. Known adjuvants include, but are not limited to, (1) aluminum hydroxide, saponine (eg QuilA), Avridine, DDA, (2) the polymers of acrylic or methaciylic acid, the copolymers of maleic anhydride and alkenyl derivative, (3) oil-in-water emulsion, water-in-oil emulsion, water-in-oil-in-water emulsion, or (4)) Montanide™Gel.

In particular, the emulsion can be based on light liquid paraffin oil; isoprenoid oil such as squalane or squalene; oil resulting from oligomerization of the alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. Oil is used with emulsifiers to form emulsions. The emulsifiers are nonionic surfactants, in particular esters of Polyoxyethylene fatty acid (e.g. oleic acid), of sorbitan, of mannide (e.g. anhydromannitol oleate), of glycerol, of polyglycerol. of propylene glycol and optionally ethoxylated oleic, isostearic, ricinoleic or hydroxy-stearic acids; ethers of fatty alcohols and polyhydric alcohols (e.g. oleyl alcohol), and polyoxypropylene-polyoxyethylene block copolymers, in particular the Pluronic® products, especially L121 (See Hunter et al., The Theory and Practical Application of Adjuvants (Ed. Stewart-Tull, D. E. S.). John Wiley and Sons, NY, pp 51-94 (1995) and Todd et al., Vaccine 15:564-570 (1997).).

In particular, adjuvant compounds are the polymers of acrylic or methacrylic acid which are cross-finked, with polyalkenyl ethers of sugars or polyalcohols. These compounds are known by the term carbomer.

Preferably, the adjuvant selected in the present disclosure is Montanide™ Gel.

The present disclosure also relates to a method for preparing the vaccine composition, comprising: step (1) respectively proliferating porcine circovirus type 3 SG strain or a culture thereof and porcine circovirus type 2 HH3 stain or a culture thereof; step (2) inactivating the porcine circovirus type 3 SG strain or a culture thereof and porcine circovirus type 2 HH3 stain or a culture thereof proliferated in step (1); step (3) proportionally mixing the inactivated porcine circovirus type 3 SG strain or a culture thereof and the inactivated porcine circovirus type 2 HH3 stain or a culture thereof, which is then added with an adjuvant and emulsified.

The present disclosure may further incorporate additional agents into the compositions of the present disclosure. For example, the composition of the present disclosure may further comprise the following agents, such as: drugs, immuno stimulants (e.g. α-interferon, β-interferon, γ-interferon, granulocyte-macrophage colony stimulating factor (GM-CSF), macrophage colony stimulating factor (M-CSF) and interleukin 2 (IL2)), antioxidants, surfactants, colorants, volatile oils, buffers, dispersants, propellants and preservatives. To prepare such compositions, methods well known in the art can be used.

The vaccine composition according to the disclosure may be prepared as an oral dosage form or a parenteral dosage form.

Preferred are parenteral dosage forms which can be administered via intradermal, intramuscular, intraperitoneal, intravenous, subcutaneous, intranasal or epidural routes.

The present disclosure also relates to a use of the above vaccine composition in preparing a medicine for preventing and/or treating diseases associated with porcine circovirus infection, wherein the diseases associated with the porcine circovirus infection are related diseases caused by single infection or mixed infection of porcine circovirus type 3 and different gene subtypes of PCV2.

The term "diseases associated with mixed infection of porcine circovirus" as used herein is used to refer to diseases caused by mixed infection of porcine circovirus type 3 and porcine circovirus type 2. Non-exhaustive examples include but are not limited to postweaning multisystemic wasting syndrome, porcine dermatitis and nephropathy syndrome, reproductive disorders, and inflammatory responses to the heart and multiple systems.

The term "preventing and/or treating" when referring to a mixed infection of porcine circovirus type 3 and porcine circovirus type 2 means inhibiting replication of porcine circovirus type 3 and porcine circovirus type 2, inhibiting transmission of porcine circovirus type 3 and porcine circovirus type 2, or preventing colonization of porcine circovirus type 3 and porcine circovirus type 2 in their host, and alleviating the symptoms of a disease or condition of porcine circovirus type 3 and type 2 infection. If the viral load is reduced, the condition is reduced and/or the food intake and/or growth is increased, then the prevention and/or treatment is considered to be effective.

As an embodiment of the present invention, in the vaccine composition of the present invention, the gene subtypes of PCV2 are PCV2a, PCV2b, PCV2d and PCV2new gene subtypes.

The vaccine composition of the present invention can provide effective protection against PCV3 and different gene subtypes of PCV2, expand the application range of the vaccine, and can prevent and/or treat single infection and mixed infection of PCV3 and different gene subtypes of PCV2.

As an embodiment of the present invention, in the vaccine composition of the present invention, the diseases associated with porcine circovirus infection include postweaning multisystemic wasting syndrome, porcine dermatitis and nephropathy syndrome, reproductive disorders, and inflammatory responses to the heart and multiple systems.

The description of the present invention is further provided as follows with reference to the specific embodiments, and features and advantages of the present invention will become more apparent from the following description. However, these embodiments are only exemplary, but not forming any limitation to the scope of the present invention. It should be understood by a person skilled in the art that modifications or alternatives to details and forms of the technical solution of the present invention without deviation from the spirit and scope of the present invention will be allowed, while those modification and alternatives should all fall within the scope of the present invention.

The chemical reagents used in the embodiments of the present invention are all analytical reagents and purchased from Sinopharma.

The experimental methods are conventional methods unless specified otherwise; the biomaterials are commercially available unless otherwise specified.

Example 1 Isolation and Identification of Porcine Circovirus Type 3

1. Source of Tissue Sample

In a domestic commercial farm, compared with the historical average values, the sow mortality rate increased by 9.4%, the conception rate decreased by 1.2%, and the rate of mummified fetuses was increased by 8.2%. Clinically, the affected sows showed symptoms of anorexia, multifocal papules, spots and dermatitis on the skin surface. Mummified fetuses of different gestational ages were found for aborted sows, which are consistent with the symptoms of PCV2-related abortion. Although the overall clinical manifestations and abortion symptoms observed in sows were consistent with reproductive failure caused by porcine circovirus type 2, the results of immunohistochemical analysis and quantitative PCR for different tissues of all the sows, including kidney, lymph nodes, lungs, skin, and stillbirth, show negative for PCV2, PRRSV, PPV, CSFV, and *Mycoplasma hyopneumoniae*. In order to further find out the reasons, the sample of each tissue were selected for isolation of pathogens.

2. Isolation and Cultivation of Virus Strains

The tissue sample was added to DMEM medium at a ratio of 1:10 (by volume), and grounded to prepare tissue suspension. The tissue suspension was centrifuged at 12000 r/min for 15 min after three repeated freeze-thaw cycles, and the supernatant was collected. After filtration of the supernatant through a 0.22 μm filter, the filtrate was passaged on PK15 cells, cultured at 37° C. for 1 h, then the culture medium was replaced with DMEM medium containing 2% of Newborn Calf Serum, and cultured at 37° C. for 5 days. The virus-containing culture solution was harvested, and after two freeze-thaw cycles of the culture solution, the virus was harvested.

3. Identification of Virus Species by PCR and Sequencing Analysis

The virus culture of the above step was taken, and the nucleic acid of the virus sample was extracted with a nucleic acid extraction kit, and PCR amplification was performed using a circovirus-specific primer. The result showed that a 2000 bp target band was amplified by PCR. The PCR product was sent to a sequencing company for determination of nucleotide sequence, and the result of sequencing was subjected to phylogenetic analysis. The results showed that both of the whole genome sequence and the amino acid sequence of the strain shared less than 50% identity to those of any other reported circoviruses. According to the standard from the International Committee on Taxonomy of Viruses, ICTV, members in the same species of the genus Circovirus should share >75% nt-identity over their entire genome, and >70% aa-identity in the Cap protein. It is therefore confirmed as a new species in the genus Circovirus, and the third type of circovirus found on pigs.

Example 2 Screening of Porcine Circovirus Type 3 Vaccine Strain

Specific primers were designed according to the above-mentioned isolated porcine circovirus type 3 (PCV3). By quantitative PCR analysis of 235 samples suspected to be positive for PCV3 collected from all over the country, 121 strains of PCV3 viruses were screened and isolated. As to these 121 strains, the identity of genomic nucleotide sequences between the different strains was as high as 98.9-99.6%, and the identity of amino acid sequence of Cap protein was as high as 97.7-99.5%. After the animal pathogenicity test and immunogenicity test, a strain of PCV3 strain with strong pathogenicity, good immunogenicity and broad protective ability was screened out. This strain of porcine circovirus type 3 was named porcine circovirus type 3 SG strain and submitted for deposition.

Example 3 Pathogenicity Test of Porcine Circovirus Type 3 SG Strain 10 healthy piglets negative for PCV2, PCV3 antigens and antibodies by ELISA, which were 28-30 days old, were randomly divided into two groups, 5 piglets/group, and the first group was challenged with PCV3 SG strain (including $10^{5.0}$ $TCID_{50}$/piglet), by intramuscular injection; the second group, i.e. the blank control group was inoculated with DMEM medium, and the piglets of each group were kept in isolation. After the challenge, the piglets in each group were continuously observed and evaluated according to their clinical symptoms, pathological changes and detection of virus. The detailed results are shown in Table 1.

TABLE 1

Results of pathogenicity test on piglets of porcine circovirus type 3 SG strain

| Group | No. | Clinical symptoms | Pathological changes | Detection of virus | Incidence rate |
|---|---|---|---|---|---|
| 1 | 1A | Body temperature increased to above 40.5° C. for 5 days, loss of appetite, depression, rough hair coat, emaciation and low growth rate | Lung consolidation, lymphadenopathy, and kidney necrosis | Positive | 100% (5/5) |
| | 1B | Body temperature increased to above 40.5° C. for 3 days, loss of appetite, depression, rough hair coat, emaciation and low growth rate | Lung consolidation, lymphadenopathy, and kidney necrosis | Positive | |
| | 1C | Body temperature increased to above 40.5° C. for 4 days, loss of appetite, depression, rough hair coat, emaciation and low growth rate | Lung consolidation, lymphadenopathy, and kidney necrosis | Positive | |
| | 1D | Body temperature increased to above 40.5° C. for 5 days, loss of appetite, depression, rough hair coat, emaciation and low growth rate | Lung consolidation, lymphadenopathy, and kidney necrosis | Positive | |
| | 1E | Body temperature increased to above 40.5° C. for 3 days, loss of appetite, depression, rough hair coat, emaciation and low growth rate | Lung consolidation, lymphadenopathy, and kidney necrosis | Positive | |
| 2 | 2A | No abnormality was found | No abnormality was found | Negative | 0% (0/5) |
| | 2B | No abnormality was found | No abnormality was found | Negative | |
| | 2C | No abnormality was found | No abnormality was found | Negative | |

TABLE 1-continued

| Results of pathogenicity test on piglets of porcine circovirus type 3 SG strain | | | | | |
|---|---|---|---|---|---|
| Group | No. | Clinical symptoms | Pathological changes | Detection of virus | Incidence rate |
| | 2D | No abnormality was found | No abnormality was found | Negative | |
| | 2E | No abnormality was found | No abnormality was found | Negative | |

The results showed that, for all the piglets in the challenge group, they all had a persistent high temperature of above 40.5° C. for 3 to 5 days, with loss of appetite, depression, rough hair coat, emaciation and low growth rate, necropsy results showed different levels of lung consolidation, lymphadenopathy, and kidney necrosis, and PCR detection of each viscera tissue confirmed that the porcine circovirus type 3 virus can be isolated again; while for the blank control group, no abnormality was found. The results showed that the porcine circovirus type 3 SG strain of the present disclosure can cause the onset of disease after being inoculated into the piglets, clinically characterized as a typical porcine circovirus infection.

Example 4 Preparation of Porcine Circovirus Type 3 SG Strain Antigen

The cultures of different passages of the porcine circovirus type 3 SG strain screened in Example 2 were inoculated into a monolayer of PK15 passage cells at 1% (VAT) of the amount of the liquid virus medium, and adsorbed at 37° C. for 30 minutes, then added with the cell maintenance solution and incubated at 37° C. The cells were observed 1 to 2 times a day, and the cells grew well. After the cells were cultured at 36 to 37° C. for 4 to 7 days, the cell cultures were harvested, and the harvested cell cultures were taken freeze-thaw cycles 2-3 times, and the virus solution was harvested to determine the virus titer. The virus solution was filtered through a hollow fiber (0.5 μm to 2 μm) filter column to remove cell debris, and then inactivated by adding 0.1% to 0.2% formaldehyde solution at 37° C. for 24 hours, and the completely inactivated virus antigen was used for prepare vaccines.

Example 5 Isolation and Identification of Porcine Circovirus Type 2

1. Source of Tissue Sample

In a pig farm in China that have been vaccinated with commercial PCV2 vaccines, there was a sporadic phenomenon of sow abortion and increased mummified fetuses. Affected sows exhibited symptoms of anorexia, and mummified fetuses of different gestational ages were found for aborted sows, consistent with the symptoms of PCV2-related abortion. PCV2 was found positive by immunohistochemical analysis and quantitative PCR. PCV2 was still detected from the affected pig tissue after the PCV2 commercial vaccine was immunized. The reason is worthy of further investigation. In order to further find out the reasons, the sample of each tissue were selected for isolation of pathogens.

2. Isolation and Cultivation of Virus Strains

The tissue sample was added to DMEM medium at a ratio of 1:10 (by volume), and grounded to prepare tissue suspension. The tissue suspension was centrifuged at 12000 r/min for 15 min after three repeated freeze-thaw cycles, and the supernatant was collected. After filtration of the supernatant through a 0.22 μm filter, the filtrate was passaged on PK15 cells, cultured at 37° C. for 1 h, then the culture medium was replaced with DMEM medium containing 2% of Newborn Calf Serum, and cultured at 37° C. for 5 days. The virus-containing culture solution was harvested, and after two freeze-thaw cycles, the virus was harvested.

3. Identification of Virus Species by PCR and Sequencing Analysis

The virus culture of the above step was taken, and the nucleic acid of the virus sample was extracted with a nucleic acid extraction kit, and PCR amplification was performed using a PCV2-specific primer. The result showed that a 1.7 kbp target band was amplified by PCR. The PCR product was sent to a sequencing company for determination of nucleotide sequence, and the result of sequencing was subjected to phylogenetic analysis. The results showed that the whole genome sequence of the virus strain shared less than 96% identity to those of any other PCV2s already reported, and the whole amino acid sequence of the virus strain shared less than 94% identity to those of any other PCV2s already reported. After further analysis, the strain was a gene subtype between PCV2b and PCV2d, with mutation or recombination of different gene subtypes in ORF2 gene, belonging to a new PCV2 gene subtype in genetic evolution analysis.

Example 6 Screening of Porcine Circovirus Type 2 Vaccine Strain

Specific primers were designed according to the above-mentioned isolated porcine circovirus type 2. By quantitative PCR analysis of 42 samples suspected to be positive for PCV2 collected from pig farms all over the country which have been vaccinated with commercial PCV2 vaccine but still with a sporadic outbreak of PCV related diseases, 16 strains of PCV2 viruses were screened and isolated. Among these 16 strains, the identity of genomic nucleotide sequence was as high as 99.6-100%, and the identity of amino acid sequence of Cap protein was as high as 99.5-100%, and these 16 strains belonged to one gene subtype after further analysis. After the animal pathogenicity test and immunogenicity test, a strain of PCV2 strain with strong pathogenicity, good immunogenicity and broad protective ability was screened out. This strain of porcine circovirus type 2 was named porcine circovirus type 2 HH3 strain and submitted for deposition.

Example 7 Pathogenicity Test of Porcine Circovirus Type 2 HH3 Strain 10 healthy piglets negative for PCV2, PCV3 antigens and antibodies by ELISA, which were 28-30 days old, were randomly divided into two groups (i.e. the third group and the fourth group), 5 piglets/group, and the third group was challenged with PCV2 HH3 strain (including $10^{5.0}$ $TCID_{50}$/piglet), by intramuscular injection;

the fourth group, i.e. the blank control group was inoculated with DMEM medium, and the piglets of each group were kept in isolation. After the challenge, the piglets in each group were continuously observed and evaluated according to their clinical symptoms, pathological changes and detection of virus. The detailed results are shown in Table 2.

TABLE 2

Results of pathogenicity test of porcine circovirus type 2 HH3 strain

| Group | No. | Clinical symptoms | Pathological changes | Detection of virus | Incidence rate |
|---|---|---|---|---|---|
| 3 | 3A | Body temperature increased to above 40.5° C. for 4 days, loss of appetite, depression, rough hair coat, emaciation and low growth rate | Lung consolidation, lymphadenopathy, and kidney necrosis | Positive | 100% (5/5) |
| | 3B | Body temperature increased to above 40.5° C. for 4 days, loss of appetite, depression, rough hair coat, emaciation and low growth rate | Lung consolidation, lymphadenopathy, and kidney necrosis | Positive | |
| | 3C | Body temperature increased to above 40.5° C. for 3 days, loss of appetite, depression, rough hair coat, emaciation and low growth rate | Lung consolidation, lymphadenopathy, and kidney necrosis | Positive | |
| | 3D | Body temperature increased to above 40.5° C. for 5 days, loss of appetite, depression, rough hair coat, emaciation and low growth rate | Lung consolidation, lymphadenopathy, and kidney necrosis | Positive | |
| | 3E | Body temperature increased to above 40.5° C. for 4 days, loss of appetite, depression, rough hair coat, emaciation and low growth rate | Lung consolidation, lymphadenopathy, and kidney necrosis | Positive | |
| 4 | 4A | No abnormality was found | No abnormality was found | Negative | 0% (0/5) |
| | 4B | No abnormality was found | No abnormality was found | Negative | |
| | 4C | No abnormality was found | No abnormality was found | Negative | |
| | 4D | No abnormality was found | No abnormality was found | Negative | |
| | 4E | No abnormality was found | No abnormality was found | Negative | |

The results showed that, for all the piglets in the challenge group, they all had a persistent high temperature of above 40.5° C. for 3 to 5 days, with loss of appetite, depression, rough hair coat, emaciation and low growth rate, necropsy results showed different levels of lung consolidation, lymphadenopathy, and kidney necrosis, and PCR detection of each viscera tissue confirmed that the porcine circovirus type 2 virus can be isolated again; while for the blank control group, no abnormality was found. The results showed that the porcine circovirus type 2 HH3 strain of the present disclosure can cause the onset of disease after being inoculated into the piglets, clinically characterized as a typical porcine circovirus infection.

Example 8 Preparation of Porcine Circovirus Type 2 HH3 Strain Antigen

The cultures of different passages of the porcine circovirus type 2 HH3 strain screened in Example 6 were inoculated into a monolayer of PK15 passage cells at 1% (VAT) of the amount of the liquid virus medium, and adsorbed at 37° C. for 30 minutes, then added with the cell maintenance solution and incubated at 37° C. The cells were observed 1 to 2 times a day, and the cells grew well. After the cells were cultured at 36 to 37° C. for 4 to 7 days, the cell cultures were harvested, and the harvested cell cultures were taken freeze-thaw cycles 2-3 times, and the virus solution was harvested to determine the virus titer. The virus solution was filtered through a hollow fiber (0.5 μm to 2 μm) filter column to remove cell debris, and then inactivated by adding 0.1% to 0.2% formaldehyde solution at 37° C. for 24 hours, and the completely inactivated virus antigen was used for prepare vaccines.

Example 9 Preparation of Inactivated Bivalent Vaccine Against Porcine Circovirus Type 3 and Porcine Circovirus Type 2

The inactivated antigen of the porcine circovirus type 3 SG strain prepared in Example 4 was mixed with the inactivated antigen of the porcine circovirus type 2 HH3 strain prepared in Example 8 at a certain ratio, followed by being slowly added to the water-soluble adjuvant Gel adjuvant (SEPPIC, France), and the mixture was continuously stirred and mixed thoroughly for 12 minutes by an emulsifying machine at 800 rpm. The specific formulation of the vaccine is shown in Table 3.

TABLE 3

Formulation and contents of inactivated bivalent vaccine against porcine circovirus type 3 and porcine circovirus type 2

| Component | Vaccine 1 | Vaccine 2 | Vaccine 3 | Vaccine 4 | Vaccine 5 |
|---|---|---|---|---|---|
| PCV3 antigen ($TCID_{50}$/ml) | $10^{5.0}$ | $10^{6.0}$ | $10^{7.0}$ | $10^{7.0}$ | — |
| PCV2 antigen ($TCID_{50}$/ml) | $10^{5.0}$ | $10^{6.0}$ | $10^{7.0}$ | — | $10^{7.0}$ |
| Gel adjuvant (V/V) | 10% | 10% | 10% | 10% | 10% |

Example 10 Immunogenicity Test of Inactivated Bivalent Vaccine Against Porcine Circovirus Type 3 and Porcine Circovirus Type 2

50 healthy piglets negative for PCV2, PCV3 antigens and antibodies by ELISA, which were 28-30 days old, were randomly divided into 10 groups, 5 piglets/group, and were immunized with the inactivated bivalent vaccine against porcine circovirus type 3 and porcine circovirus type 2 prepared in Example 9. groups 5 to 6 were immunized with vaccine 1, groups 7 to 8 were immunized with vaccine 2, groups 9 to 10 were immunized with vaccine 3, groups 11 to 12 were immunized with vaccines 4 and 5 respectively, and groups 13-14, as control groups, were not immunized. Each immunization group was injected with 2 ml/piglet of vaccine, and the control groups were inoculated with 2 ml/piglet of DMEM medium. On day 28 after immunization, the piglets in groups 5, 7, 9, 11 and 13 were challenged with $10^{5.0}$ $TCID_{50}$/piglet of porcine circovirus type 3 SG strain, while the piglets in groups 6, 8, 10, 12 and 14 were challenged with $10^{5.0}$ $TCID_{50}$/piglet of porcine circovirus type 2 HH3 strain. After the challenge, each piglet was observed continuously and evaluated according to their clinical symptoms, pathological changes and results of detection of virus. The detailed results are shown in Table 4.

TABLE 4

Results of immunogenicity test of inactivated bivalent vaccine against porcine circovirus type 3 and porcine circovirus type 2

| Group | Clinical symptoms | Pathological changes | Detection of virus (positive rate) | Protection rate |
|---|---|---|---|---|
| 5 | No abnormality was found | No abnormality was found | 0% (0/5) | 100% (5/5) |
| 6 | No abnormality was found | No abnormality was found | 0% (0/5) | 100% (5/5) |
| 7 | No abnormality was found | No abnormality was found | 0% (0/5) | 100% (5/5) |
| 8 | No abnormality was found | No abnormality was found | 0% (0/5) | 100% (5/5) |
| 9 | No abnormality was found | No abnormality was found | 0% (0/5) | 100% (5/5) |
| 10 | No abnormality was found | No abnormality was found | 0% (0/5) | 100% (5/5) |
| 11 | No abnormality was found | No abnormality was found | 0% (0/5) | 100% (5/5) |
| 12 | No abnormality was found | No abnormality was found | 0% (0/5) | 100% (5/5) |
| 13 | Body temperature increased to above 40.5° C. for 3-5 days, loss of appetite, depression, rough hair coat, emaciation and low growth rate | All showed different levels of lung consolidation, lymphadenopathy, kidney necrosis | 100% (5/5) | 0% (0/5) |
| 14 | Body temperature increased to above 40.5° C. for 3-5 days, loss of appetite, depression, rough hair coat, emaciation and low growth rate | All showed different levels of lung consolidation, lymphadenopathy, kidney necrosis | 100% (5/5) | 0% (0/5) |

The results showed that the inactivated bivalent vaccine against porcine circovirus type 3 and porcine circovirus type 2 could provide 100% (5/5) protection rate for piglets after one-time immunization, while all control piglets were ill after the challenge. This shows that the inactivated bivalent vaccine against porcine circovirus type 3 and porcine circovirus type 2 provided by the disclosure can provide excellent protection.

Example 11 Broad-Spectrum Protection Test of Inactivated Bivalent Vaccine Against Porcine Circovirus Type 3 and Porcine Circovirus Type 2

100 healthy piglets negative for PCV2, PCV3 antigens and antibodies by ELISA, which were 28-30 days old, were randomly divided into 20 groups, 5 piglets/group, and groups 15 to 24 were immunized with the inactivated vaccine 1 prepared in Example 9, groups 25-34, as control groups, were not immunized. Each of the immunization groups was injected with 2 ml/piglet of the vaccine, and each of the control groups was inoculated with 2 ml/piglet of DMEM medium. The challenge was carried out on day 28 after immunization, and groups 15 and 25 were challenged with the porcine circovirus gene subtype 2a HN06 virulent strain newly isolated from Henan Province, China; groups 16 and 26 were challenged with the porcine circovirus gene subtype 2b JS04 virulent strain newly isolated from Jiangsu Province, China; groups 17 and 27 were challenged with the porcine circovirus gene subtype 2d JL13 virulent strain isolated from Jilin Province, China; groups 18 and 28 were challenged with the porcine circovirus gene type 2new CQ14 virulent strain isolated from Chongqing City, China; groups 19 and 29 were challenged with the porcine circovirus subtype 2new GD15 virulent strain newly isolated from Guangdong Province, China; groups 20 and 30 were challenged with the porcine circovirus type 3 HN12 virulent strain newly isolated from Henan Province, China; groups 21 and 31 were challenged with the porcine circovirus type 3 JS08 virulent strain newly isolated from Jiangsu Province, China; groups 22 and 32 were challenged with the porcine circovirus type 3 JL11 virulent strain isolated from Jilin Province, China; groups 23 and 33 were challenged with the porcine circovirus type 3 CQ04 virulent strain isolated from Chongqing City, China; groups 24 and 34 were challenged with the porcine circovirus type 3 GD05 virulent strain newly isolated from Guangdong Province, China; the dose for challenging in each group was $10^{5.0}$ $TCID_{50}$/piglet. After the challenge, each piglet was continuously observed, and evaluated according to their clinical symptoms, pathological changes and detection of virus. The detailed results are shown in Tables 5-6.

TABLE 5

Results of broad-spectrum protection test against PCV2 infection for inactivated bivalent vaccine against porcine circovirus type 3 and porcine circovirus type 2

| Group | Clinical symptoms | Pathological changes | Detection of virus (positive rate) | Protection rate |
|---|---|---|---|---|
| 15 | No abnormality was found | No abnormality was found | 0% (0/5) | 100% (5/5) |
| 16 | No abnormality was found | No abnormality was found | 0% (0/5) | 100% (5/5) |
| 17 | No abnormality was found | No abnormality was found | 0% (0/5) | 100% (5/5) |
| 18 | No abnormality was found | No abnormality was found | 0% (0/5) | 100% (5/5) |
| 19 | No abnormality was found | No abnormality was found | 0% (0/5) | 100% (5/5) |
| 25 | Body temperature increased to above 40.5° C. for 3 days, loss of appetite, depression, rough hair coat, emaciation and low growth rate | All showed different levels of lung consolidation, lymphadenopa thy, kidney necrosis | 100% (5/5) | 0% (0/5) |
| 26 | Body temperature increased to above 40.5° C. for 3-4 days, loss of appetite, depression, rough hair coat, emaciation and low growth rate | All showed different levels of lung consolidation, lymphadenopa thy, kidney necrosis | 100% (5/5) | 0% (0/5) |
| 27 | Body temperature increased to above 40.5° C. for 3-4 days, loss of appetite, depression, rough hair coat, emaciation and low growth rate | All showed different levels of lung consolidation, lymphadenopa thy, kidney necrosis | 100% (5/5) | 0% (0/5) |
| 28 | Body temperature increased to above 40.5° C. for 3-5 days, loss of appetite, depression, rough | All showed different levels of lung consolidation, lymphadenopa | 100% (5/5) | 0% (0/5) |

TABLE 5-continued

| Results of broad-spectrum protection test against PCV2 infection for inactivated bivalent vaccine against porcine circovirus type 3 and porcine circovirus type 2 | | | | |
|---|---|---|---|---|
| Group | Clinical symptoms | Pathological changes | Detection of virus (positive rate) | Protection rate |
| | hair coat, emaciation and low growth rate | thy, kidney necrosis | | |
| 29 | Body temperature increased to above 40.5° C. for 3-5 days, loss of appetite, depression, rough hair coat, emaciation and low growth rate | All showed different levels of lung consolidation, lymphadenopa thy, kidney necrosis | 100% (5/5) | 0% (0/5) |

According to the results, for groups 25-29, the challenging control groups, all piglets showed different levels of clinical symptoms such as temperature increased to above 40.5° C. for 3-5 days, loss of appetite, depression, rough hair coat, emaciation and low growth rate etc. and all the necropsy showed different levels of lung consolidation, lymphadenopathy, kidney necrosis, and PCR detection of each viscera tissue confirmed that the porcine circovirus type 2 virus can be isolated again; while for groups 15-19, the immunization groups, after the challenge, no abnormal clinical symptoms were found, and no abnormalities were observed in all tissues and organs after necropsy, PCR detection was performed on each viscera tissue, indicating negative for PCV2. The above results indicate that the inactivated bivalent vaccine against porcine circovirus type 3 and porcine circovirus type 2 provided by the present disclosure can provide effective and complete immune protection for pigs against challenge by porcine circovirus type 2 from different geographical origins and different gene subtypes of porcine circovirus type 2 after one-time immunization, no PCV2 strain that was used in the challenge could be detected from various organ tissues.

TABLE 6

| Results of broad-spectrum protection test against PCV3 infection for inactivated bivalent vaccine against porcine circovirus type 3 and porcine circovirus type 2 | | | | |
|---|---|---|---|---|
| Group | Clinical symptoms | Pathologic al changes | Detection of virus ( positive rate) | Protection rate |
| 20 | No abnormality was found | No abnormality was found | 0% (0/5) | 100% (5/5) |
| 21 | No abnormality was found | No abnormality was found | 0% (0/5) | 100% (5/5) |
| 22 | No abnormality was found | No abnormality was found | 0% (0/5) | 100% (5/5) |
| 23 | No abnormality was found | No abnormality was found | 0% (0/5) | 100% (5/5) |
| 24 | No abnormality was found | No abnormality was found | 0% (0/5) | 100% (5/5) |
| 30 | Body temperature increased to above 40.5° C. for 3-5 days, loss of appetite, depression, rough hair coat, emaciation and low growth rate | All showed different levels of lung consolidation, lymphadenopathy, kidney necrosis | 100% (5/5) | 0% (0/5) |
| 31 | Body temperature increased to above 40.5° C. for 3-5 days, loss of appetite, depression, rough hair coat, emaciation and low growth rate | All showed different levels of lung consolidation, lymphadenopathy, kidney necrosis | 100% (5/5) | 0% (0/5) |
| 32 | Body temperature increased to above 40.5° C. for 3-5 days, loss of appetite, depression, rough hair coat, emaciation and low growth rate | All showed different levels of lung consolidation, lymphadenopathy, kidney necrosis | 100% (5/5) | 0% (0/5) |

TABLE 6-continued

Results of broad-spectrum protection test against PCV3 infection for inactivated bivalent vaccine against porcine circovirus type 3 and porcine circovirus type 2

| Group | Clinical symptoms | Pathologic al changes | Detection of virus ( positive rate) | Protection rate |
|---|---|---|---|---|
| 33 | Body temperature increased to above 40.5° C. for 3-5 days, loss of appetite, depression, rough hair coat, emaciation and low growth rate | All showed different levels of lung consolidation, lymphadenopathy, kidney necrosis | 100% (5/5) | 0% (0/5) |
| 34 | Body temperature increased to above 40.5° C. for 3-5 days, loss of appetite, depression, rough hair coat, emaciation and low growth rate | All showed different levels of lung consolidation, lymphadenopathy, kidney necrosis | 100% (5/5) | 0% (0/5) |

According to the results, for groups 30-34, the challenging control groups, all piglets showed different levels of clinical symptoms such as temperature increased to above 40.5° C. for 3-5 days, loss of appetite, depression, rough hair coat, emaciation and low growth rate etc. and all the necropsy showed different levels of lung consolidation, lymphadenopathy, kidney necrosis, and PCR detection of each viscera tissue confirmed that the porcine circovirus type 3 virus can be isolated again; while for groups 20-24, the immunization groups, after the challenge, no abnormal clinical symptoms were found, and no abnormalities were observed in all tissues and organs after necropsy, PCR detection was performed on each viscera tissue, indicating negative for PCV3. The above results indicate that the inactivated bivalent vaccine against porcine circovirus type 3 and porcine circovirus type 2 provided by the present disclosure can provide effective and complete immune protection for pigs against challenge by porcine circovirus type 3 from different geographical origins and different gene subtypes of porcine circovirus type 3 after one-time immunization, no PCV3 strain that was used in the challenge could be detected from various organ tissues.

The above results showed that the vaccine compositions of the present disclosure have a broad spectrum of immunogenicity and provide complete protection against strains of porcine circovirus type 3 and porcine circovirus type 2 from different geographic sources.

Example 12 Protection Test Against Mixed Infection for Inactivated Bivalent Vaccine Against Porcine Circovirus Type 3 and Porcine Circovirus Type 2

20 healthy piglets negative for PCV2, PCV3 antigens and antibodies by ELISA, which were 28-30 days old, were randomly divided into 4 groups, 5 piglets/group. Group 35 was immunized with vaccine 1 prepared in Example 9, group 36 was immunized with vaccine 4 prepared in Example 9, group 37 was immunized with vaccine 5 prepared in Example 9, and group 38 as a challenging control group, was not immunized. Each immunization group was injected with 2 ml/piglet of vaccine, and the control groups were inoculated with 2 ml/piglet of DMEM medium. On day 28 after immunization, all the groups were challenged with $10^{5.0}$ $TCID_{50}$/piglet of the mixed virus solution of porcine circovirus type 3 SG strain and porcine circovirus type 2 HH3 strain. After the challenge, each piglet was observed continuously and evaluated according to their clinical symptoms, pathological changes and results of detection of virus. The detailed results are shown in Table 7.

TABLE 7

Result of protection test against mixed infection for inactivated bivalent vaccine against porcine circovirus type 3 and porcine circovirus type 2

| Group | clinical symptoms | pathological changes | protection rate |
|---|---|---|---|
| 35 | No abnormality was found | No abnormality was found | 100% (5/5) |
| 36 | Body temperature increased to above 40.5° C. for 3-5 days, loss of appetite, depression, rough hair coat, emaciation and low growth rate | All showed different levels of lung consolidation, lymphadenopathy, kidney necrosis | 0% (0/5) |
| 37 | Body temperature increased to above 40.5° C. for 3-5 days, loss of appetite, depression, rough hair coat, emaciation and low growth rate | All showed different levels of lung consolidation, lymphadenopathy, kidney necrosis | 0% (0/5) |
| 38 | Body temperature increased to above 40.5° C. for 5 days, loss | All showed different levels of lung | 0% (0/5) |

TABLE 7-continued

| Result of protection test against mixed infection for inactivated bivalent vaccine against porcine circovirus type 3 and porcine circovirus type 2 | | | |
|---|---|---|---|
| Group | clinical symptoms | pathological changes | protection rate |
| | of appetite, depression, rough hair coat, emaciation and low growth rate | consolidation, lymphadenopathy, kidney necrosis | |

According to the results, for group 38, the challenging control group, all piglets showed different levels of clinical symptoms such as temperature increased to above 40.5° C. for 5 days, loss of appetite, depression, rough hair coat, emaciation and low growth rate etc. and all the necropsy showed different levels of lung consolidation, lymphadenopathy and kidney necrosis; while for group 35, which was an immunization group, after the challenge, no abnormal clinical symptoms were found, and no abnormalities were observed in all tissues and organs after necropsy. Groups 36 and 37, which were immunization groups, could not effectively prevent the mixed infection of PCV2 and PCV3, and remained in the onset state. It is indicated that the porcine circovirus type 3 and type 2 inactivated vaccine provided by the invention can provide effective and complete immune protection against combined challenge by PCV2 and PCV3, after one-time immunization.

Example 13 Application Test of Inactivated Bivalent Vaccine Against Porcine Circovirus Type 3 and Porcine Circovirus Type 2

In a domestic commercial farm, compared with the historical average values, the sow mortality rate increased by 9.8%, the conception rate decreased by 1.2%, and the rate of mummified fetuses was increased by 8.6%. Clinically, the affected sows showed symptoms of anorexia, multifocal papules, spots and dermatitis on the skin surface. Mummified fetuses of different gestational ages were found for aborted sows. 36 pregnant sows with clinical manifestations were randomly divided into two groups: group A, group B, 18 pigs/group. Group A was an immunization group, which was immunized with inactivated vaccine 1 prepared in Example 9, and group B was a blank control group. The immunization group was injected with 2 ml/pig of vaccine, and the blank control group was inoculated with 2 ml/pig of DMEM medium. The results of sow fertility for the two groups were counted. These results are shown in Table 8.

TABLE 8

| Statistical results of sow fertility for the immunization group and the blank control group | | | | | | |
|---|---|---|---|---|---|---|
| Group | No. | Number of healthy piglets | Number of mummified fetuses | Number of weak piglets | Average number of healthy piglets born | Healthy rate |
| A | A-1 | 12 | 0 | 0 | 11.7 | 99.5% |
| | A-2 | 12 | 0 | 0 | | (211/212) |
| | A-3 | 11 | 0 | 1 | | |
| | A-4 | 13 | 0 | 0 | | |
| | A-5 | 12 | 0 | 0 | | |
| | A-6 | 12 | 0 | 0 | | |
| | A-7 | 12 | 0 | 0 | | |
| | A-8 | 10 | 0 | 0 | | |
| | A-9 | 11 | 0 | 0 | | |
| | A-10 | 10 | 0 | 0 | | |
| | A-11 | 13 | 0 | 0 | | |
| | A-12 | 13 | 0 | 0 | | |
| | A-13 | 12 | 0 | 0 | | |
| | A-14 | 12 | 0 | 0 | | |
| | A-15 | 12 | 0 | 0 | | |
| | A-16 | 11 | 0 | 0 | | |
| | A-17 | 11 | 0 | 0 | | |
| | A-18 | 12 | 0 | 0 | | |
| B | B-1 | 7 | 1 | 3 | 6.9 | 58.8% |
| | B-2 | 7 | 2 | 2 | | (124/211) |
| | B-3 | 8 | 1 | 2 | | |
| | B-4 | 8 | 1 | 3 | | |
| | B-5 | 9 | 1 | 3 | | |
| | B-6 | 0 | 13 | 0 | | |
| | B-7 | 10 | 0 | 2 | | |
| | B-8 | 8 | 1 | 3 | | |
| | B-9 | 7 | 2 | 2 | | |
| | B-10 | 9 | 0 | 3 | | |
| | B-11 | 8 | 0 | 3 | | |

TABLE 8-continued

| Statistical results of sow fertility for the immunization group and the blank control group | | | | | | |
|---|---|---|---|---|---|---|
| Group | No. | Number of healthy piglets | Number of mummified fetuses | Number of weak piglets | Average number of healthy piglets born | Healthy rate |
| | B-12 | 8 | 1 | 2 | | |
| | B-13 | 9 | 1 | 2 | | |
| | B-14 | 9 | 0 | 3 | | |
| | B-15 | 7 | 2 | 3 | | |
| | B-16 | 0 | 11 | 0 | | |
| | B-17 | 10 | 0 | 2 | | |
| | B-18 | 0 | 12 | 0 | | |

The results showed that the immunization groups had no abnormality in fertility, producing healthy piglets with an average of 11.7 piglets/litter, and the healthy rate was as high as 99.5%. However, the control group showed obvious mummified fetuses and weak piglets, and the average number of healthy piglets was 6.9 per litter, and the healthy rate was 58.8%, and three sows aborted with the whole litter having mummified fetuses. The difference between the immunization groups and the control groups was significant.

The results in Table 8 demonstrate that the inactivated bivalent vaccine against porcine circovirus type 3 and porcine circovirus type 2 of the present disclosure has a good immunoprotective effect on sows infected with porcine circovirus, and can protect sows which have been infected with PCV.

At the same time, the piglets produced from the blank control group B were isolated and feed by litter, and 15 litters were divided into two groups: group B1 (a total of 12 litters of piglets, including litters B-1 to B-13, except litter B-6 due to the whole litter having mummified fetuses), group B2 (a total of 3 litters, including litters B-14 to B-18, except litter B-16 and B-18 due to the whole litters having mummified fetuses), the piglets in group B1 were immunized with inactivated vaccine 1 prepared in Example 9 before breastfeeding, group B2 was a blank control group. The immunization group was injected with 2 ml/piglet of vaccine, and the blank control group was inoculated with 2 ml/piglet of DMEM medium. Each piglet was continuously observed and judged according to the clinical symptoms, pathological changes and virus detection of each piglet. The detailed results are shown in Table 9.

TABLE 9

| Immune protection test of inactivated bivalent vaccine against porcine circovirus type 3 and porcine circovirus type 2 on piglets | | | | | |
|---|---|---|---|---|---|
| Group | | clinical symptoms | pathological changes | detection of virus (positive rate) | protection rate |
| B1 | B-1 | No abnormality was found | No abnormality was found in necropsy of one randomly selected piglet | The tissue sample from the piglet subjected to necropsy was determined as negative | 100% (7/7) |
| | B-2 | No abnormality was found | No abnormality was found in necropsy of one randomly selected piglet | The tissue sample from the piglet subjected to necropsy was determined as negative | 100% (7/7) |
| | B-3 | No abnormality was found | No abnormality was found in necropsy of one randomly selected piglet | The tissue sample from the piglet subjected to necropsy was determined as negative | 100% (8/8) |
| | B-4 | No abnormality was found | No abnormality was found in necropsy of one randomly selected piglet | The tissue sample from the piglet subjected to necropsy was determined as negative | 100% (8/8) |
| | B-5 | No abnormality was found | No abnormality was found in necropsy of one randomly selected piglet | The tissue sample from the piglet subjected to necropsy was determined as negative | 100% (9/9) |
| | B-7 | No abnormality was found | No abnormality was found in | The tissue sample from the | 100% (10/10) |

TABLE 9-continued

Immune protection test of inactivated bivalent vaccine against porcine circovirus type 3 and porcine circovirus type 2 on piglets

| Group | | clinical symptoms | pathological changes | detection of virus (positive rate) | protection rate |
|---|---|---|---|---|---|
| | | | necropsy of one randomly selected piglet | piglet subjected to necropsy was determined as negative | |
| | B-8 | No abnormality was found | No abnormality was found in necropsy of one randomly selected piglet | The tissue sample from the piglet subjected to necropsy was determined as negative | 100% (8/8) |
| | B-9 | No abnormality was found | No abnormality was found in necropsy of one randomly selected piglet | The tissue sample from the piglet subjected to necropsy was determined as negative | 100% (7/7) |
| | B-10 | No abnormality was found | No abnormality was found in necropsy of one randomly selected piglet | The tissue sample from the piglet subjected to necropsy was determined as negative | 100% (9/9) |
| | B-11 | No abnormality was found | No abnormality was found in necropsy of one randomly selected piglet | The tissue sample from the piglet subjected to necropsy was determined as negative | 100% (8/8) |
| | B-12 | No abnormality was found | No abnormality was found in necropsy of one randomly selected piglet | The tissue sample from the piglet subjected to necropsy was determined as negative | 100% (8/8) |
| | B-13 | No abnormality was found | No abnormality was found in necropsy of one randomly selected piglet | The tissue sample from the piglet subjected to necropsy was determined as negative | 100% (9/9) |
| B2 | B-14 | Body temperature increased to above 40.5° C. for 5 days, loss of appetite, depression, rough hair coat, emaciation and low growth rate; 4 piglets died. | All showed different levels of lung consolidation, lymphadenopathy, kidney necrosis | 100% (9/9) | 0% (0/9) |
| | B-15 | Body temperature increased to above 40.5° C. for 4 days, loss of depression, rough hair coat, emaciation and low growth rate; 3 piglets died. | All showed different levels of lung consolidation, lymphadenopathy, kidney necrosis | 100% (7/7) | 0% (0/7) |
| | B-17 | Body temperature increased to above 40.5° C. for 5 days, loss of | All showed different levels of lung consolidation, lymphadenopathy, kidney necrosis | 100% (7/7) | 0% (0/10) |

TABLE 9-continued

Immune protection test of inactivated bivalent vaccine against porcine circovirus type 3 and porcine circovirus type 2 on piglets

| Group | clinical symptoms | pathological changes | detection of virus (positive rate) | protection rate |
|---|---|---|---|---|
| | appetite, depression, rough hair coat, emaciation and low growth rate; 3 piglets died. | | | |

According to the results, for the immunization group, no abnormal clinical symptoms were found, and no abnormalities were observed in all tissues and organs after necropsy, PCR detection was performed on each viscera tissue of piglets, indicating negative for PCV3 and PCV2; while for the piglets in the control group, they all showed different levels of clinical symptoms such as temperature increased to above 40.5° C. for 5 days, loss of appetite, depression, rough hair coat, emaciation and low growth rate etc, a part of piglets died, and all the necropsy showed pathological changes like different levels of lung consolidation, lymphadenopathy, and kidney necrosis, and PCR detection of each viscera tissue confirmed that the porcine circovirus type 3 and porcine circovirus type 2 viruses can be isolated again.

Since PCV can be vertically transmitted in the herd, the results in Table 9 demonstrate that the bivalent vaccine against porcine circovirus type 3 and porcine circovirus type 2 in the present disclosure has a good immunoprotective effect on piglets infected with porcine circovirus type 3 and porcine circovirus type 2 after one-time immunization, and can also protect piglets that have been infected with PCV3 and PCV2 with a protection rate of 100%.

The foregoing descriptions are merely preferred examples of the present disclosure and are not intended to limit the present disclosure in any form. Although the present disclosure has been disclosed by way of preferred examples, it is to be understood that the disclosure is not limited thereto. A person skilled in the art can make some equivalent variations or modifications to the above-disclosed technical content without departing from the scope of the technical solutions of the present disclosure to obtain equivalent examples. Simple modifications, equivalent changes and modifications made to the above examples according to the technical essence of the present disclosure all fall within the scope of the technical solutions of the present disclosure without departing from the contents of the technical solutions of the present disclosure.

The invention claimed is:

1. A vaccine composition for preventing and/or treating porcine circovirus infection, wherein the vaccine composition comprises an immunogenic amount of porcine circovirus type 3 antigen, an immunogenic amount of porcine circovirus type 2 antigen and an adjuvant, wherein the porcine circovirus type 3 antigen is an antigen of a porcine circovirus type 3 SG strain deposited with the CCTCC under the accession number V201712; and the porcine circovirus type 2 antigen is an antigen of a porcine circovirus type 2 HH3 strain deposited with the CCTCC under the accession number V201726.

2. The vaccine composition according to claim 1, wherein the antigen of the porcine circovirus type 3 SG strain is an inactivated whole-virus antigen of the porcine circovirus type 3 SG strain or a culture thereof, wherein the culture of the porcine circovirus type 3 SG strain is a culture which has been subcultured for more than one passage;

wherein the antigen of the porcine circovirus type 2 HH3 strain is an inactivated whole-virus antigen of the porcine circovirus type 2 HH3 strain or a culture thereof, and wherein the culture of the porcine circovirus type 2 HH3 strain is a culture which has been subcultured for more than one passage.

3. The vaccine composition according to claim 2, wherein the culture of the porcine circovirus type 3 SG strain is a culture which has been subcultured for more than five passages, and the culture of the porcine circovirus type 2 HH3 strain is a culture which has been subcultured for more than five passages.

4. The vaccine composition according to claim 2, wherein the culture of the porcine circovirus type 3 SG strain is a culture which has been subcultured for 5 to 55 passages, and the culture of the porcine circovirus type 2 HH3 strain is a culture which has been subcultured for 5 to 48 passages.

5. The vaccine composition according to claim 2, wherein the inactivated whole-virus antigen content of the porcine circovirus type 3 SG strain or the culture thereof is equal to or more than $10^{5.0}$ $TCID_{50}$/ml before inactivation, and the inactivated whole-virus antigen content of the porcine circovirus type 2 HH3 strain or the culture thereof is equal to or more than $10^{5.0}$ $TCID_{50}$/ml before inactivation.

6. The vaccine composition according to claim 2, wherein the inactivated whole-virus antigen content of the porcine circovirus type 3 SG strain or the culture thereof is within a range of $10^{5.0}$ to $10^{7.0}$ $TCID_{50}$/ml before inactivation, and the inactivated whole-virus antigen content of the porcine circovirus type 2 HH3 strain or the culture thereof is within a range of $10^{5.0}$ to $10^{7.0}$ $TCID_{50}$/ml before inactivation.

7. The vaccine composition according to claim 2, wherein the inactivated whole-virus antigen content of the porcine circovirus type 3 SG strain or the culture thereof is $10^{6.0}$ $TCID_{50}$/ml before inactivation, and the inactivated whole-virus antigen content of the porcine circovirus type 2 HH3 strain or the culture thereof is $10^{6.0}$ $TCID_{50}$/ml before inactivation.

8. The vaccine composition according to claim 1, wherein the adjuvant comprises white oil or mineral oil; aluminum hydroxide or aluminum phosphate; or a polymer-based adjuvant that contains gel particles of sodium polyacrylate in water, carbomer, squalane or squalene, ISA206 adjuvant, or saponin, and the adjuvant is used in an amount of 5 to 20% by volume.

9. The vaccine composition according to claim 8, wherein the adjuvant is a polymer-based adjuvant comprising gel particles of sodium polyacrylate in water.

10. The vaccine composition according to claim 8, wherein the adjuvant is used in an amount of 10% by volume.

11. A method for the prevention and/or treatment of a porcine circovirus type 3 and/or porcine circovirus type 2 related disease in a subject, comprising administering an effective amount of the vaccine composition according to claim 1 to the subject.

12. The method according to claim 11, wherein the disease is selected from the group consisting of postweaning multisystemic wasting syndrome, porcine dermatitis and nephropathy syndrome, reproductive disorders, and inflammatory responses to the heart and multiple systems.

* * * * *